US012643843B2

(12) United States Patent
Boehm et al.

(10) Patent No.: US 12,643,843 B2
(45) Date of Patent: Jun. 2, 2026

(54) DEHYDROGENATION AND PYROLYSIS PRODUCT RECOVERY WITH A COMMON REFRIGERANT

(71) Applicant: UOP LLC, Des Plaines, IL (US)

(72) Inventors: Ernest J. Boehm, Hanover Park, IL (US); Sudipta K. Ghosh, Gurgaon (IN); Prashant Balyan, Gurgaon (IN); Xin X. Zhu, Long Grove, IL (US); Kyle Cuellar, Fulshear, TX (US)

(73) Assignee: UOP LLC, Rosemont, IL (US)

( * ) Notice: Subject to any disclaimer, the term of this patent is extended or adjusted under 35 U.S.C. 154(b) by 260 days.

(21) Appl. No.: 18/510,244

(22) Filed: Nov. 15, 2023

(65) Prior Publication Data

US 2024/0166582 A1      May 23, 2024

Related U.S. Application Data

(60) Provisional application No. 63/384,931, filed on Nov. 23, 2022.

(51) Int. Cl.
*C07C 7/09* (2006.01)
*B01D 3/00* (2006.01)
(Continued)

(52) U.S. Cl.
CPC .............. *C07C 7/09* (2013.01); *B01D 3/007* (2013.01); *B01D 3/143* (2013.01); *B01J 6/008* (2013.01)

(58) Field of Classification Search
CPC .......... C07C 7/09; C07C 5/333; C07C 7/005; C07C 7/04; C07C 9/04; C07C 9/06; C07C 9/08; C07C 11/06; B01D 3/007;

B01D 3/143; B01J 6/008; B01J 2208/0053; B01J 2208/00539; B01J 2219/0002; B01J 2219/00159; B01J 2219/00162; F25J 2200/40; F25J 3/0238; F25J 2200/74; F25J 3/0219; F25J 3/0233; F25J 3/0242; F25J 3/0252; F25J 2200/70; F25J 220/78; F25J 220/94; F25J 2205/04; F25J 2210/02;
(Continued)

(56) References Cited

U.S. PATENT DOCUMENTS

| | | | | | |
|---|---|---|---|---|---|
| 4,629,484 A | * | 12/1986 | Kister | .................... | F25J 3/0252 |
| | | | | | 62/622 |
| 6,271,433 B1 | * | 8/2001 | Keady | .................... | F25J 3/0242 |
| | | | | | 585/803 |

(Continued)

FOREIGN PATENT DOCUMENTS

| | | | | | |
|---|---|---|---|---|---|
| CN | 111747813 A | * | 10/2020 | ............. | C07C 5/327 |
| CN | 111807921 A | | 10/2020 | | |
| CN | 212870441 U | | 4/2021 | | |

OTHER PUBLICATIONS

Translation of CN-111747813-A (Year: 2020).*
Search Report and Written Opinion for PCT/US2023/080916 dated Mar. 22, 2024.

*Primary Examiner* — Ali Z Fadhel
(74) *Attorney, Agent, or Firm* — Paschall & Associates, LLC; James C. Paschall

(57)      ABSTRACT

A process and apparatus cool a pyrolyzed stream and a dehydrogenated stream in respective cold boxes by use of a refrigerant compressed with a common compressor. The refrigerant is compressed and used to cool a pyrolysis cold box and a dehydrogenation cold box.

18 Claims, 1 Drawing Sheet

(51) Int. Cl.
  B01D 3/14                (2006.01)
  B01J 6/00                (2006.01)
(58) Field of Classification Search
  CPC .. F25J 2210/06; F25J 2210/12; F25J 2210/62;
          F25J 2215/62; F25J 2215/64; F25J
        2230/008; F25J 2230/60; F25J 2240/02;
          F25J 2260/02; F25J 2270/12; F25J
                  2270/66; F25J 2270/904
  See application file for complete search history.

(56)                  References Cited

U.S. PATENT DOCUMENTS

| 7,219,513 B1 * | 5/2007 | Mostafa | F25J 3/0209 |
|---|---|---|---|
| | | | 62/620 |
| 2003/0060642 A1 * | 3/2003 | Shah | C07D 301/10 |
| | | | 549/518 |
| 2003/0192341 A1 * | 10/2003 | Wei | F25J 3/0233 |
| | | | 62/612 |
| 2012/0000244 A1 | 1/2012 | Sechrist et al. | |
| 2012/0137726 A1 * | 6/2012 | Currence | F25J 3/0238 |
| | | | 62/611 |
| 2014/0260421 A1 * | 9/2014 | Lee | F25J 3/0238 |
| | | | 62/636 |
| 2018/0073803 A1 * | 3/2018 | Schwint | F25J 3/0238 |
| 2019/0352240 A1 * | 11/2019 | Jo | B01D 53/04 |
| 2020/0109893 A1 * | 4/2020 | Ducote, Jr. | F25J 3/0645 |
| 2020/0165177 A1 * | 5/2020 | Höfel | C10G 9/00 |
| 2021/0130263 A1 * | 5/2021 | Jo | C01B 3/56 |
| 2021/0180862 A1 * | 6/2021 | Haney | C10G 9/36 |
| 2026/0002729 A1 * | 1/2026 | Guvelioglu | F25J 3/0238 |

* cited by examiner

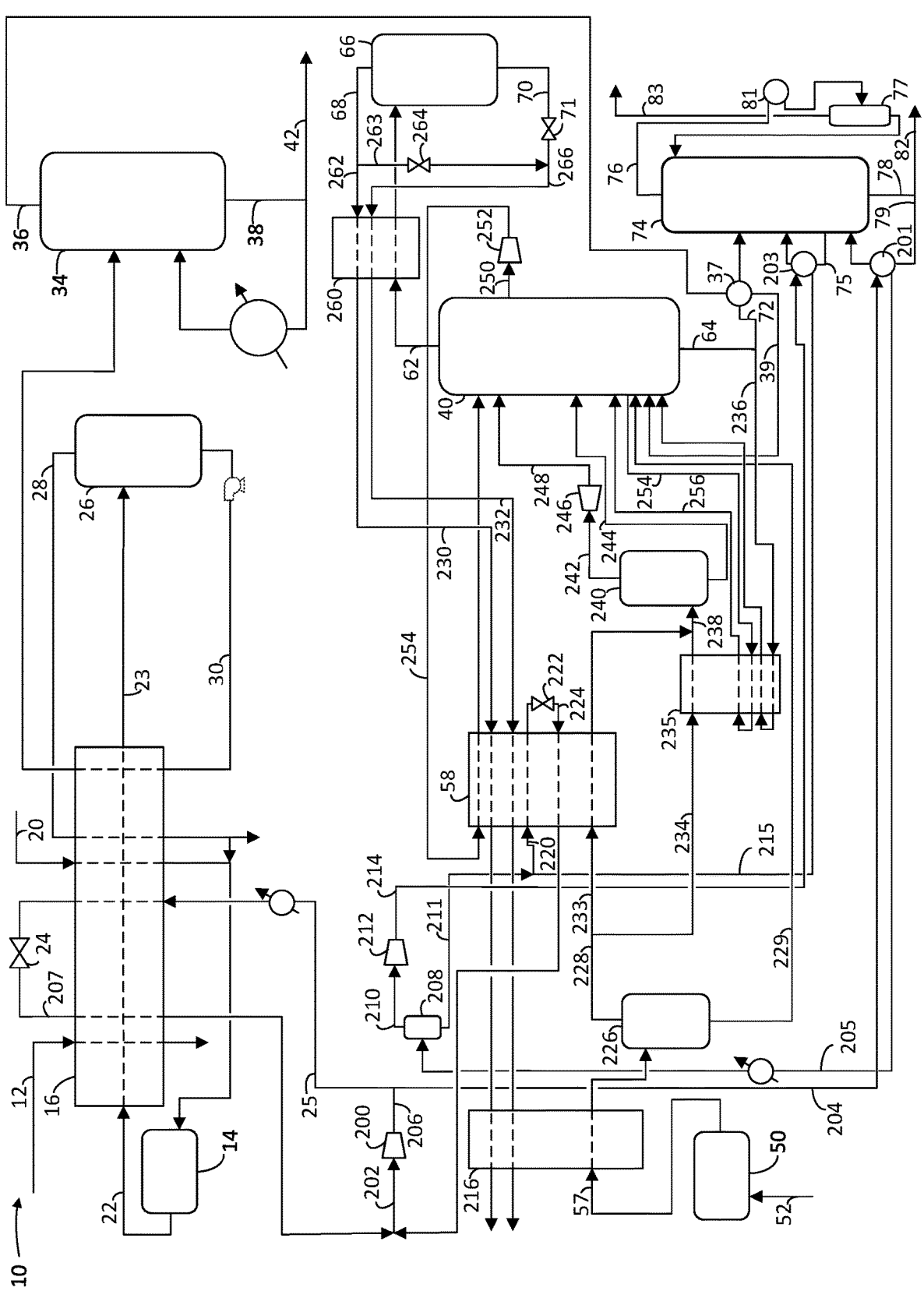

DEHYDROGENATION AND PYROLYSIS PRODUCT RECOVERY WITH A COMMON REFRIGERANT

FIELD

The field relates to recovery of light olefins, ethylene and propylene, and also recovery and separation of light component by-products such as hydrogen, methane, ethane and propane. Particularly, the field relates to recovery of ethylene and propylene from pyrolysis effluent and dehydrogenation effluent.

BACKGROUND

Dehydrogenation of propane and steam cracking of saturated and predominantly paraffinic hydrocarbons such as naphtha, butanes, propane and ethane are important commercial hydrocarbon conversion processes because they produce light olefins which are building blocks for polyolefins and polymers whose demand is growing. In particular, demand of ethylene and propylene in the petrochemical industry has grown substantially due to their use as precursors in the production of polyethylene and polypropylene for many commercial products. One route for producing propylene is the dehydrogenation of propane. The main products from a steam cracker are ethylene and propylene; however other byproducts such as hydrogen, methane and other heavier hydrocarbons may be further processed for other petrochemical processes.

A process for the conversion of paraffins to olefins via propane dehydrogenation process involves passing a propane feed stream over a highly selective catalyst to dehydrogenate the propane to propylene in the dehydrogenation reactor effluent. Cooling and separation of the dehydrogenation reactor effluent into a hydrocarbon-rich fraction and a hydrogen-rich vapor fraction, part of which is non-recycled net gas, is provided in a cryogenic separation system that requires refrigeration for cooling the process streams in order to separate hydrogen from light hydrocarbon liquid. The conventional cryogenic separation system cools process streams alone to remove hydrogen from light hydrocarbons. However, further fractionation is needed to separate the C2-material from the C3 hydrocarbons in the dehydrogenation effluent in a deethanizer column which also typically requires a refrigeration package.

The great bulk of the ethylene consumed in the production of plastics and petrochemicals such as polyethylene is produced by the thermal cracking or pyrolysis of hydrocarbons. Pyrolysis also produces substantial propylene that is useful in the plastics industry for making polypropylene. Steam is usually mixed with the feed stream to the cracking furnace to reduce the hydrocarbon partial pressure and enhance olefin yield and to reduce the formation and deposition of carbonaceous material in the cracking reactors. The process is therefore often referred to a steam cracking or pyrolysis.

Steam cracking generates lower value by-products such as pyrolysis gasoline (pygas) and fuel oil (pyoil). Pygas contains large proportions of paraffins and aromatics. The resulting paraffins include normal and non-normal paraffins which can be recovered or further processed. Aromatics are very stable and difficult to crack in a steam cracker. The paraffinic side chains can be removed, but this leads to the production of multi-ring aromatics which increases the yield of low-value fuel oil. Normal paraffins more selectively pyrolyze to olefins than non-normal paraffins.

Improvements in separation systems are necessary to recover light olefins from dehydrogenation and pyrolysis effluents as well as other valuable by products such as hydrogen and methane.

SUMMARY

We have discovered an improved process for cooling a pyrolyzed stream and a dehydrogenated stream in respective cold boxes by use of a refrigerant compressed with a common compressor. The refrigerant is compressed and used to cool a pyrolysis cold box and a dehydrogenation cold box.

These and other features, aspects, and advantages of the present disclosure are further explained by the following detailed description, drawing and appended claims.

BRIEF DESCRIPTION OF THE DRAWING

The FIGURE is a schematic representation of the process and apparatus of the present disclosure.

DEFINITIONS

The following detailed description is merely exemplary in nature and is not intended to limit the application and uses of the embodiment described. Furthermore, there is no intention to be bound by any theory presented in the preceding background or the following detailed description.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "bypass" means that the object is out of downstream communication with a bypassing subject at least to the extent of bypassing.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

As used herein, the term "predominant" or "predominate" means greater than 50%, suitably greater than 75% and preferably greater than 90%.

The term "$C_x$" is to be understood to refer to molecules having the number of carbon atoms represented by the subscript "x". Similarly, the term "$C_{x-}$" refers to molecules that contain less than or equal to x and preferably x and less carbon atoms. The term "$C_{x+}$" refers to molecules with more than or equal to x and preferably x and more carbon atoms.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Unless otherwise indicated, overhead lines and bottom lines refer to the net lines from the column downstream of the reflux or reboil to the column. Alternatively, a stripping stream may be used for heat input near the bottom of the column.

As used herein, the term a component "rich stream" or a "stream rich" in a component means that the stream identified as rich coming out of a vessel has a greater concentration of the component than the feed to the vessel.

As used herein, the term a component "lean stream" or a "stream lean" in a component means that the stream identified as lean coming out of a vessel has a lower concentration of the component than the feed to the vessel.

DETAILED DESCRIPTION

The disclosure is a process and apparatus which integrates the recovery of propylene from a propane dehydrogenation reactor and a pyrolysis reactor by using a common refrigerant. The process and apparatus may also use a common compression train. We have found by utilizing a propane dehydrogenation reactor with a pyrolysis reactor additional production of propylene can accompany abundant ethylene production by pyrolysis.

The process and apparatus 10 shown in FIG. 1, processes effluents from two conversion units, a propane dehydrogenation reactor 14 and a pyrolysis reactor 50. A propane stream in line 12 is prepared for charge to a propane dehydrogenation reactor 14. The propane stream comprises propane and may comprise other light paraffins such as ethane, normal butane, isobutane, pentane or iso-pentane. In some embodiments, the propane stream comprises at least one other paraffin having 2 to 30 carbon atoms.

The propane stream in line 12 is cooled in a PDH cold box 16 or may be bypassed around the cold box and transported to a depropanizer fractionation column that is not shown for purification before it is warmed or cooled slightly to approximately 25° C. to 50° C. and preferably 35°C to 40° C. in the dehydrogenation cold box 16 in line 20 and charged to the propane dehydrogenation reactor 14.

In the dehydrogenation reactor 14, propane is dehydrogenated to produce propylene. A dehydrogenation catalyst is used in a dehydrogenation reaction to catalyze the dehydrogenation of propane. The conditions in the dehydrogenation reactor may include a temperature of about 500 to about 800° C., a pressure of about 40 to about 310 kPa and a catalyst to oil ratio of about 5 to about 100.

The dehydrogenation reaction may be conducted in a fluidized manner such that gas, which may comprise the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated in a regenerator. The regenerator may combust coke from the dehydrogenation catalyst and fuel gas to ensure sufficient enthalpy in the dehydrogenation reactor to promote the endothermic reaction.

The dehydrogenation catalyst selected should minimize cracking reactions and favor dehydrogenation reactions. Suitable catalysts for use herein include an active metal which may be dispersed in a porous inorganic carrier material such as silica, alumina, silica alumina, zirconia, or clay. An exemplary embodiment of a catalyst includes alumina or silica-alumina containing gallium, a noble metal, and an alkali or alkaline earth metal.

The catalyst support comprises a carrier material, a binder and an optional filler material to provide physical strength and integrity. The carrier material may include alumina or silica-alumina. Silica sol or alumina sol may be used as the binder. The alumina or silica-alumina generally contains alumina of gamma, theta and/or delta phases. The catalyst support particles may have a nominal diameter of about 20 to about 200 micrometers with the average diameter of about 50 to about 150 micrometers. Preferably, the surface area of the catalyst support is about 85 to about 140 $m^2/g$.

The fluidized dehydrogenation catalyst may comprise a dehydrogenation metal on a support. The dehydrogenation metal may be a one or a combination of transition metals. A noble metal may be a preferred dehydrogenation metal such as platinum or palladium. Gallium is an effective metal for paraffin dehydrogenation. Metals may be deposited on the catalyst support by impregnation or other suitable methods or included in the carrier material or binder during catalyst preparation.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of about 0.001% to about 10 wt % metals may be incorporated into the dehydrogenation catalyst. In the case of the noble metals, it is preferred to use about 10 parts per million (ppm) by weight to about 600 ppm by weight noble metal. More preferably it is preferred to use about 10 to about 100 ppm by weight noble metal. The preferred noble metal is platinum. Gallium should be present in the range of 0.3 wt % to about 3 wt %, preferably about 0.5 wt % to about 2 wt %. Alkali and alkaline earth metals may be present in the range of about 0.05 wt % to about 1 wt %.

Regenerated catalyst may be contacted with the propane stream perhaps with a fluidizing gas to lift the propane stream and dehydrogenation catalyst up a riser while dehydrogenation occurs. Above the riser spent dehydrogenation catalyst and propylene product may be separated by a centripetal separation device. Propylene product gas may be quenched with a cooling fluid to prevent over reaction to undesired by-products. Separation of the propylene product may include quench contacting and fractionation to produce a propylene product stream in line 22.

The paraffin dehydrogenation reactor 14 may alternatively employ a catalytic moving bed reactor. The reactor section may comprise several radial flow reactors in parallel or series heated by charge and interstage heaters. The propane stream perhaps with added hydrogen flows in each dehydrogenation reactor from a screened center pipe through an annular dehydrogenation catalyst bed to an outer effluent annulus. Flow may be in the reverse fashion. The dehydrogenation catalyst may comprise a noble metal or mixtures thereof, a modifier selected from the group consisting of alkali metals or alkaline-earth metals and mixtures thereof, a component selected from the group consisting of tin, germanium, lead, indium, gallium, thallium, and mixtures thereof, and a porous support forming a catalyst particle. The catalyst support may comprise oil dropped alumina spheres.

Dehydrogenation conditions may include a temperature of from about 400 to about 900° C., a pressure of from about 0.01 to 10 atmospheres absolute, and a liquid hourly space velocity (LHSV) of from about 0.1 to about 100 hr$^{-1}$. The pressure in the dehydrogenation reactor is maintained as low as practicable, consistent with equipment limitations, to maximize chemical equilibrium advantages. Spent dehydrogenation catalyst in the annular catalyst bed may be withdrawn from the bottom of the bed, forwarded to a regenerator to combust coke from the catalyst with air at about 450 to about 600° ° C. Noble metal on the catalyst may be redispersed by an oxyhalogenation process, dried and returned to the top of the dehydrogenation catalyst bed as regenerated dehydrogenation catalyst.

The dehydrogenated stream in line 22 may comprise light hydrocarbons and hydrogen. The propylene must be separated from other light hydrocarbons such as unreacted propane and hydrogen. Propane can be recycled to the dehydrogenation reactor for propylene production. Hydrogen is a valuable byproduct and may be used elsewhere in the refinery or in the dehydrogenation reactor 14 to control the dehydrogenation reaction.

The dehydrogenated stream in line 22 may be cooled, compressed and dried before hydrogen separation. To separate the hydrogen from the light hydrocarbons effectively, the dehydrogenated stream in line 22 is cryogenically cooled by passing it to the dehydrogenation cold box 16 to condense the hydrocarbons. In the dehydrogenation cold box 16, the dehydrogenated stream in line 22 is cooled by heat exchange with other streams including a refrigerant stream in line 25 passing through the dehydrogenation cold box 16 to provide a cooled dehydrogenated stream in line 23 which is fed to a dehydrogenation separator 26. The refrigerant stream in line 25 may have been through a first stage of compression and be at a pressure of about 1400 to about 1700 kPa. The refrigerant stream in line 25 may pass through the dehydrogenation cold box 16, then expand through an expansion valve 24 to cool the refrigerant stream by the heat of vaporization and pass back through the dehydrogenation cold box 16. The dehydrogenation cold box 16 may be in downstream communication with said dehydrogenation reactor 14.

The cooled dehydrogenated stream in line 23 is separated in the dehydrogenation separator 26 to provide a net gas overhead stream rich in hydrogen in a dehydrogenation separator overhead line 28 extending from an overhead of the dehydrogenation separator 26 and a liquid dehydrogenation stream rich in hydrocarbons in a dehydrogenation separator bottoms line 30 extending from a bottom of the separator. The dehydrogenation separator 26 may operate at a temperature between about −100° C. (−150° F.) and about 66° C. (150° F.) and more commonly between about −95° C. (−138° F.) and about −40° ° C. (−40° F.), and a gauge pressure between about 690 kPa (100 psig) and about 1.4 MPa (200 psig).

The net gas overhead stream in the separator overhead line 28 is sufficiently hydrogen pure from one stage of separation by the thorough condensation of the hydrocarbons in the dehydrogenation separator 26. The net gas overhead stream may possess a hydrogen purity of at least 94 mol %, suitably at least 95 mol %, preferably at least 96 mol % and most preferably at least 96.5 mol % molecular hydrogen. The net gas overhead stream in line 28 can be routed to the dehydrogenation cold box 16 to be heated and provide a product hydrogen stream that can be used elsewhere in the refinery or plant. The warmed net gas stream in line 28 may be provided at a temperature of about 32° C.

(90° F.) to about 60° C. (140° F.) and a gauge pressure of about 760 kPa (110 psig) to about 1.2 MPa (170 psig). A part of the hydrogen rich, net gas overhead stream in line 28 is also mixed with the propane charge stream in line 20 and charged to the dehydrogenation reactor 14, for suppressing the coke laydown reactions.

The liquid dehydrogenation stream in line 30 is rich in hydrocarbons that can be refined for valuable products. The liquid dehydrogenation stream in the dehydrogenation separator bottoms line 30 may be heated by passing it through the dehydrogenation cold box to vaporize the hydrocarbons. The vaporized hydrocarbons in line 30 cool by giving up the heat of vaporization and therefore assist in cooling the dehydrogenated stream passed through the dehydrogenation cold box 16 in line 22. The requisite heat exchange in the dehydrogenation cold box 16 occurs between the cold and the hot streams and the dehydrogenation refrigerant stream in line 25. The liquid dehydrogenated stream in line 30 is heated by passing it through the dehydrogenation cold box 16 and fed to the dehydrogenation stripping column 34.

The liquid dehydrogenation stream in line 30 comprises some light ends like methane and ethane that must be separated from larger hydrocarbons like propylene and propane. Hence, the liquid dehydrogenation stream in line 30, after heating in the dehydrogenation cold box 16 to a temperature of about 0° C. (30° F.) to about 45° C. (115° F.) is passed to a dehydrogenation stripping column 34 for fractionation. The dehydrogenated stripping column 34 separates the liquid dehydrogenated stream into a stripping overhead stream rich in methane and ethane along with slipped C3 hydrocarbons in a stripping overhead line 36 extending from an overhead of the stripping column 34 and a stripping bottoms stream in a stripping bottoms line 38 extending from a bottom of the stripping column 34 which is rich in C3 hydrocarbons. The stripping removes light ends with a limited quantity of C3 hydrocarbons in the overhead vapor. However, the C3 hydrocarbons in the stripping overhead stream are recovered in a demethanizer column 40 to which the stripping overhead stream is routed. The stripping overhead stream in line 36 is heat exchanged with a net demethanizer bottoms stream in a net demethanizer bottoms line 72 in a heat exchanger 37 to cool the stripping overhead stream to provide a cooled stripping overhead stream and heat the net demethanizer bottom stream to provide a heated net demethanizer bottoms stream. The cooled stripping overhead stream is fed as a demethanizer feed stream in a demethanizer feed line 39 to the demethanizer column 40 to remove methane and lighter gases from the stripping overhead stream. The heated net demethanizer bottoms stream in line 72 may be fed to a decthanizer column 74.

The stripping bottoms stream in the stripping bottoms line 38 is split into a reboil stream which is boiled up and returned to the paraffin dehydrogenation stripping column 34 and a net stripping bottoms stream is transported in a net stripping bottoms line 42 to a propylene-propane splitter column not shown. The stripping column 34 may operate at a bottoms temperature of about 30° C. (90° F.) to about 60° C. (140° F.) and an overhead gauge pressure of about 1.5 to about 1.9 MPa (gauge). The stripping column 34 may be in downstream communication with the dehydrogenation cold box 16 and the dehydrogenation separator 26.

The process and apparatus 10 omit a paraffin dehydrogenation deethanizer column and cryogenic cooling equipment associated therewith necessary for olefins recovery. Instead, olefins recovery can take place downstream of the pyrolysis reactor 50.

To provide sufficient cooling for the dehydrogenation cold box 16 and the pyrolysis cold box 58, a refrigerant stream in line 202 is fed to a first refrigerant compressor 200 in which it is compressed to a pressure of about 1500 kPa to about 1750 kPa in a first stage of compression to provide a first compressed refrigerant stream in line 206. The refrigerant stream may be a mixed refrigerant stream comprising nitrogen and some or all of C1 to C5 hydrocarbons. The mixed refrigerant may be a mixture of up to six components suitably selected to meet refrigeration requirements of the dehydrogenated stream and the pyrolyzed stream. The mixed refrigerant composition may comprise about 0 to about 7 mol % inert gas, about 11 to about 35 mol % methane, about 25 to about 40 mol % C2 hydrocarbon, about 20 to about 50 mol % C3 hydrocarbon and about 0 to about 15 mol % C5 hydrocarbon. The inert gas may be nitrogen, and the C5 hydrocarbon may be isopentane.

A reboil refrigerant stream in line 204 and a dehydrogenation refrigerant stream in line 25 are taken from the first compressed refrigerant stream in line 206. The reboil refrigerant stream in line 204 is heat exchanged in a deethanizer bottom reboil exchanger 201 with a decthanizer bottom reboil stream in a reboil line 79 taken from the deethanizer bottom stream in line 78 to boil up the deethanizer bottom reboil stream and cool the first compressed refrigerant stream in line 204 to provide a cooled first compressed refrigerant stream in line 205 and a boiling deethanizer bottom reboil stream which is returned to the decthanizer column. The cooled first compressed refrigerant stream in line 205 is further cooled to near ambient temperature in a cooler and is separated in a second stage separator 208. If necessary, supplemental deethanizer bottom reboiling perhaps by a low-level heat stream (not shown) may be necessary to provide sufficient heat to reboil the deethanizer bottom reboil stream in line 79 in addition to the heating provided by the first compressed refrigerant stream in line 204.

The second stage separator 208 separates the cooled first compressed refrigerant stream in line 205 into a second compression vapor stream in a second stage separator overhead line 210 and a second compression liquid stream in a second compression refrigerant bottoms line 211. The second compression liquid stream in line 211 is joined with the second compressed refrigerant stream in a second compressed refrigerant line 215.

The dehydrogenation refrigerant stream in line 25 taken from the first compressed refrigerant stream in line 206 is cooled to near ambient temperature and is transported to the dehydrogenation cold box 16 in which it is heat exchanged with the liquid dehydrogenated stream in the dehydrogenated bottom line 30 to warm the liquid dehydrogenated stream in line 30. and other streams and cool the dehydrogenation refrigerant stream in line 25. The dehydrogenation cold box 16 may be in downstream communication with the first refrigerant compressor 200. After passing through the dehydrogenation cold box 16, the cooled dehydrogenation refrigerant stream in line 25 is passed through an expansion valve 24 to vaporize the dehydrogenation refrigerant stream thereby cooling it and providing a vaporized dehydrogenation refrigerant stream in line 207. The vaporized dehydrogenation refrigerant stream in line 207 passes back through the dehydrogenation cold box 16 to further provide cooling to the streams passing therethrough including the dehydrogenated stream in line 22. A warmed vaporized dehydrogenation refrigerant stream in line 207 is returned to provide a portion of the refrigerant stream in line 202.

The second compression vapor stream in line 210 separated in the second stage separator 208 is compressed in a second compressor 212 to a pressure of about 4500 to about 5500 kPa in a second stage of compression to provide a second compressed refrigerant stream in line 214. The second compressed refrigerant stream in line 214 is heat exchanged in a decthanizer side reboil exchanger 203 with a deethanizer side reboil stream in line 75 from the decthanizer column 74 to boil up the side reboil stream and cool the second compressed refrigerant stream in line 214 and undergoing further cooling in an additional exchanger if needed (not shown) to provide a cooled second compressed refrigerant stream in line 215 and a boiling side reboil stream in line 75 which is returned to the column. The cooled second compressed refrigerant stream in line 215 is joined with the second compression liquid stream in the second stage separator bottoms line 211 to provide a total second compressed refrigerant stream in line 220.

The total second compressed refrigerant stream in line 220 is then passed to a pyrolysis cold box 58 in which it is heat exchanged with a main pyrolyzed stream in line 233 to cool the main pyrolyzed stream and other streams and also cool the total second compressed refrigerant stream. After passing through the pyrolysis cold box 58, the cooled total second compressed refrigerant stream in line 220 is passed through an expansion valve 222 to vaporize the total second compressed refrigerant stream and thereby cool it to provide a vaporized second compressed refrigerant stream in line 224. The vaporized second compressed refrigerant stream in line 224 may be passed back through the pyrolysis cold box 58 to further provide cooling to the streams passing therethrough including the main pyrolyzed stream in line 233. A warmed vaporized second compressed refrigerant stream in line 224 is returned to provide a portion of the refrigerant stream in line 202. The pyrolysis cold box 58 may be in downstream communication with the first refrigerant compressor 200 and the second refrigerant compressor 212.

A pyrolysis charge stream in charge line 52 perhaps supplemented with recycle ethane is charged to a pyrolysis reactor 50 which may be a steam cracking furnace for cracking hydrocarbons under steam to produce a pyrolyzed stream in pyrolysis line 57. The pyrolysis charge stream may optionally be in the gas phase. The pyrolysis reactor 50 may preferably be operated at a temperature of about 750° C. (1382° F.) to about 950° C. (1742° F.). The pyrolysis charge stream may be one of many feed streams that enter at the same point of the furnace, or at separate points to maximize product yields. The pyrolysis charge stream may be an ethane stream or a naphtha stream.

The pyrolyzed stream exiting the pyrolysis reactor 50 in pyrolyzed line 57 may be in a superheated state. One or more quench columns, or other devices not shown, but preferably an oil quench column and/or a water quench column, may be used for quenching the pyrolyzed stream. The pyrolyzed stream may be caustic washed in a scrubber column to remove acid gases and the scrubbed gas compressed to provide a treated pyrolyzed gas stream in line 57 before it is cooled in a pyrolysis cold box 58. The pyrolysis cold box 58 may be in downstream communication with the pyrolysis reactor 50.

Although other streams may be recovered from the pyrolysis reactor 50, the treated pyrolyzed stream in line 57 may be a gaseous pyrolyzed stream. The gaseous pyrolyzed stream may be cooled first in off-gas exchanger 216 by heat exchange with a cool net hydrogen stream in line 230 and a cool volatile methane stream in line 232 which are off gases generated in the pyrolysis reactor.

In the off-gas exchanger 216, the pyrolyzed stream is heat exchanged with a cool net hydrogen stream in line 230 and a cool volatile methane stream in line 232 to heat them and cool the pyrolyzed stream in line 57 to provide a cooled pyrolyzed stream. The cooled pyrolyzed stream in line 57 is separated in a pyrolysis separator 226 into the gaseous pyrolyzed stream in line 228 and a liquid pyrolyzed stream in line 229. The liquid pyrolyzed stream in line 229 is fed to the demethanizer column 40 to provide liquid near a bottom of the demethanizer column. The demethanizer column 40 may be in downstream communication with the dehydrogenation cold box 16, the pyrolysis cold box 58 and the stripping column 34. The demethanizer column 40 may also be in downstream communication with the paraffin dehydrogenation reactor 14 and the pyrolysis reactor 50.

The gaseous pyrolyzed stream in line 228 is divided into two streams: the main pyrolyzed stream in line 233 and a bypass pyrolyzed stream in line 234. The main pyrolyzed stream in line 233 is cooled in the pyrolysis cold box 58 by heat exchange with the total second compressed refrigerant stream in line 220 and the vaporized second compressed refrigerant stream in line 224 to provide a cooled main pyrolyzed stream in line 233 and a warmed vaporized second compressed refrigerant stream in line 224. The bypass pyrolyzed stream in line 234 is heat exchanged in the demethanizer reboiler 235 with a demethanizer bottom reboil stream in line 236 taken from the demethanized bottom stream in the demethanizer bottoms line 64 which cools the bypass pyrolyzed stream to provide a cooled bypass pyrolyzed stream in line 234 and boils up the demethanizer bottom reboil stream in line 236 which is returned boiling to the demethanizer column 40.

The demethanizer reboiler 235 is also used to provide side-reboiling to the demethanizer column. A demethanizer side reboil stream in a demethanizer side reboil line 254 from the demethanizer is drawn from a suitable tray and partially vaporized in the demethanizer reboiler 235 by heat exchange with the bypass pyrolyzed stream in bypass line 234 to provide a cooled bypass pyrolyzed stream and boils up the demethanizer side reboil stream in line 254 which is returned at least partially boiling to the demethanizer column 40 in a demethanizer side reboiling line 256. The heating in the demethanizer reboiler 235 is provided by the by the bypass pyrolyzed stream in line 234 which in turn gets further cooled thus maximizing heat exchange opportunities. The cooled bypass pyrolyzed stream in line 234 is reunited with the cooled main pyrolyzed stream in line 233 to provide a reunited pyrolyzed stream in line 238. The reunited cooled pyrolyzed stream in line 238 is then separated in a turboexpander drum 240.

The turboexpander drum 240 separates the reunited cooled pyrolyzed stream in line 238 into a gaseous reunited pyrolyzed stream in line 242 and a liquid reunited pyrolyzed stream in line 244. The gaseous cooled pyrolyzed stream is expanded in a turboexpander 246 into an expanded gaseous cooled pyrolyzed stream in line 248 thereby cooling the gaseous cooled pyrolyzed stream due to polytropic gas expansion and also generating power from the turboexpander 246. The expanded gaseous pyrolyzed stream in line 248 may be fed to the demethanizer column 40 in which it is demethanized.

The expanded gaseous pyrolyzed stream in line 248 is fed to the top of the demethanizer column 40 above the liquid reunited pyrolyzed stream in line 244. The liquid reunited pyrolyzed stream in line 244 may be fed to the demethanizer column 40 above the partially boiling demethanizer side reboil stream in the demethanizer side reboiling line 256.

The take off for the demethanizer side reboil stream in line 254 is below the feed for the demethanizer side reboiling stream in line 256 but both are above the feed elevation for the liquid pyrolyzed stream in line 229. The feed elevation for the liquid pyrolyzed stream in line 229 is above the elevation for the demethanizer feed stream in line 39. The demethanizer bottom reboiled stream in line 236 is fed to the demethanizer column at an elevation below the demethanizer feed stream in line 239.

The stripping overhead stream rich in C2- and residual C3 hydrocarbons in the stripping overhead line 36 extending from an overhead of the stripping column 34 may be heat exchanged in the heat exchanger 37 with the net demethanizer bottoms stream in the net demethanizer bottoms line 72 and fed to the demethanizer column 40. The warmed net demethanizer bottoms stream in the net demethanizer bottoms line 72 may be fed to the decthanizer column 74.

To provide further cooling and reflux for achieving the desired ethylene recovery in the demethanizer column 40, a C2 hydrocarbon lean vapor side stream from a suitable tray of the demethanizer column is taken in line 250 and may be compressed in a side compressor 252 to provide the compressed side stream in line 254. The compressed side stream in line 254 may be cooled by heat exchange with the total second compressed refrigerant stream in line 220 in the pyrolysis cold box 58 to provide a cooled compressed side stream that is refluxed to the demethanizer column 40 at an elevation above a feed of the expanded gaseous pyrolyzed stream in line 248 to the demethanizer column 40 which may be the highest feed elevation to the column. The take off for the lean vapor side stream in line 250 may be at an elevation below the feed for the expanded gaseous pyrolyzed stream in line 248 to the demethanizer column 40.

In the demethanizer column 40 the cooled stripping overhead stream in line 39 rich in C2– hydrocarbons with residual C3 hydrocarbons, the cooled pyrolyzed streams comprising the liquid pyrolyzed stream in line 229, the expanded gaseous cooled pyrolyzed stream in line 248 and the liquid reunited cooled pyrolyzed stream in line 244 are fractionated together to provide a demethanizer overhead stream rich in methane and hydrogen in the demethanizer overhead line 62 and a demethanized bottoms stream in a demethanizer bottoms line 64 which is rich in C2+ hydrocarbons. The demethanized overhead stream with very minimal ethylene loss is achieved by providing a cooled reflux and allowing slippage of a predominantly C1– stream of hydrogen and methane as a net overhead stream of the demethanizer column 40. The demethanizer overhead stream in line 62 is cooled by heat exchange with a net gas hydrogen stream in line 262 and a volatile methane stream in line 266 in a hydrogen-hydrocarbon exchanger 260 to provide a warm net hydrogen stream in line 230 and a warm volatile methane stream in line 232.

The condensed demethanized overhead stream may be separated in a hydrogen-methane separator 66 to provide a hydrogen stream in the net overhead line 68 rich in hydrogen and a net overhead liquid stream rich in methane in a hydrogen-methane separator bottoms line 70. The methane stream in the net hydrogen-methane separator bottoms line 70 may be vaporized by expansion over an expansion valve 71 to provide a gaseous methane stream. A hydrogen diversion stream in line 263 may be taken from the hydrogen stream in the net overhead line 68 to leave a net hydrogen stream in line 262. The hydrogen diversion stream in line 263 may be expanded over an expansion valve 264 and added to the expanded methane stream in the net liquid line 70 to provide a volatile methane stream in line 266. The added hydrogen will reduce the vaporization temperature of the methane in the net liquid line to increase the heat of vaporization it withdraws, thereby cooling the temperature in the hydrogen-methane separator 66 and increasing the hydrogen purity of the hydrogen stream in the net overhead line 68 from the hydrogen-methane separator.

The net hydrogen stream in line 262 and the volatile methane stream in line 266 may be warmed by heat exchange with the demethanized overhead stream in the demethanizer overhead line 62 to provide the warm net hydrogen stream in line 230 and the warm volatile methane stream in line 232, respectively. The warm net hydrogen stream in line 230 and the warm volatile methane stream in line 232 may be heat exchanged with the main pyrolyzed stream in line 233 and the total second compressed refrigerant stream in line 220 to further warm the warm net hydrogen stream and the warm volatile methane stream while cooling the main pyrolyzed stream in line 233 and the total second compressed refrigerant stream in line 220. The pyrolyzed stream in line 57 is then able to further warm the warm net hydrogen stream in line 230 and the warm volatile methane stream in line 232 and cool the pyrolyzed stream in line 57 to provide the cooled pyrolyzed stream fed to the pyrolysis separator 226.

The demethanizer bottom reboil stream in line 64 is split into a reboil bottom stream in line 236 which is boiled up and returned to the demethanizer column 40 and a net demethanized bottom stream in a net demethanizer bottoms line 72. The reboil bottom stream in line 236 is boiled up by heat exchange with a bypass pyrolyzed stream in line 234 in the demethanizer reboiler 235 to provide a boiling reboil bottom stream in line 236 and a cooled bypass pyrolyzed stream in line 234. The stripping overhead stream in line 36 is heat exchanged in the heat exchanger 37 to warm the net demethanized stream in line 72 and cool the stripping overhead stream in line 36 before the net demethanized stream is fed to a deethanizer column 74.

The deethanizer column 74 fractionates the net demethanizer bottoms stream in line 72 into a deethanizer overhead stream in line 76 rich in C2 hydrocarbons and a deethanized bottoms stream in line 78 rich in C3+ hydrocarbons. The deethanizer overhead stream in line 76 is condensed in a deethanizer condenser 81. The condensed overhead stream in line 76 is fed to a deethanizer receiver 77 in which it is separated into a liquid reflux stream that is refluxed back to the deethanizer column 74 and a net overhead stream in line 83 which may be further processed such as in a C2 splitter column and/or a selective hydrogenation reactor that are not shown in the drawing.

The deethanized bottom stream in line 78 provides a bottoms reboil stream in line 79 which is reboiled by heat exchange in a reboiler 201 with the first compressed refrigerant stream in line 204 and fed back boiling to the deethanizer column 74. The deethanized bottom stream in line 78 also provides a net deethanized bottom stream that may be fed to a depropanizer column in line 82. The deethanizer column 74 operates at an overhead temperature of about −10° C. (15° F.) to about −32° C. (−25° F.) and a bottoms gauge pressure of about 1.1 MPa (160 psig) to about 2.5 MPa (360 psig).

The disclosed process and apparatus meet the refrigeration needs of both propane dehydrogenation cold box 16 and the pyrolysis cold box 58 using a single refrigerant. The mixed refrigerant system is optimal from energy standpoint and also the integrated approach leads to reduction of equipment count and capex reduction. This integrated process and apparatus 10 achieves hydrogen recovery at sufficient purity to be processed in a pressure swing adsorption unit, methane at high purity with respect to ethylene and also a very high degree of ethylene and propylene recovery. These objectives are achieved minimizing equipment count of exchangers, separation vessels and reduced energy usage.

EXAMPLE

We conducted a cost analysis for a conventional process in which a multistage cascade refrigeration system utilizing ethylene and propylene refrigeration loops for pyrolysis and dehydrogenation recovery including a methane compressor for pyrolysis recovery and compared it to an integrated process employing a mixed refrigerant compressor for both dehydrogenation and pyrolysis with propylene refrigeration for pyrolysis. The integrated case also employed a methane compressor, an off-gas compressor, a PSA feed gas compressor and a turbo-expander. The analysis was performed for a 500 kiloton propylene per annum dehydrogenation unit and a 500 kiloton propylene and 1500 kiloton ethylene per annum pyrolysis unit.

We found the integrated process reduced compressor power by over 7% resulting in a $9 to 12 M/year reduction in utility cost which is about 8 to about 11% of the base case. Operational savings from the integration are shown in Table 1.

TABLE 1

| Operational Expense | Savings per year ($) | Utility |
|---|---|---|
| Utility Cost | 9-12M | |
| Carbon Dioxide Emission | 7M | 70 kilometric tons/year |
| Cooling Water | | 100 m³/h |

Capital expense savings provided by the integrated process versus the base process are shown in Table 2.

TABLE 2

| Equipment | Base Process | Integrated Process |
|---|---|---|
| Drums | 21 | 9 |
| Compressor stages | 11 | 8 |
| Expanders | 0 | 1 |
| Plate Heat Exchangers | 10 | 4 |
| Shell and Tube and Air Cooler Heat Exchangers | 14 | 7 |
| Total | 56 | 29 |

It was unexpected that equipment count by integration could be cut by almost half. Capital expense was reduced by $44 M which is about 18% of the base case.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for cooling streams comprising cooling a dehydrogenated stream in a dehydrogenation cold box to provide a cooled dehydrogenated stream; cooling a pyrolyzed stream in a pyrolysis cold box to provide a cooled pyrolyzed stream; providing a refrigerant stream to the dehydrogenation cold box and to the pyrolysis cold box. An embodiment of the disclosure is one, any or all of prior embodiments in this paragraph up through the first embodiment in this paragraph further comprising compressing the refrigerant stream in a first compressor to provide a first compressed refrigerant stream taking a dehydrogenation refrigerant stream from the first compressed refrigerant stream, and heat exchanging the dehydrogenated stream with the dehydrogenation refrigerant stream An embodiment of the disclosure is one, any or all of prior embodiments in this paragraph up through the first embodiment in this paragraph further comprising taking a second compression refrigerant stream from the first compressed refrigerant stream and compressing the second compression refrigerant stream to provide a second compressed refrigerant stream and heat exchanging the pyrolyzed stream with the second compressed refrigerant stream. An embodiment of the disclosure is one, any or all of prior embodiments in this paragraph up through the first embodiment in this paragraph further comprising separating the cooled dehydrogenated stream into a net gas stream and a liquid dehydrogenation stream and stripping the liquid dehydrogenation stream to provide a stripping overhead stream. An embodiment of the disclosure is one, any or all of prior embodiments in this paragraph up through the first embodiment in this paragraph further comprising separating the cooled pyrolyzed stream into a gaseous cooled pyrolyzed stream, expanding the gaseous cooled pyrolyzed stream into an expanded gaseous cooled pyrolyzed stream and demethanizing the expanded gaseous cooled pyrolyzed stream and the stripping overhead stream in a demethanizer column. An embodiment of the disclosure is one, any or all of prior embodiments in this paragraph up through the first embodiment in this paragraph further comprising separating the cooled pyrolyzed stream into a gaseous cooled pyrolyzed stream, expanding the gaseous cooled pyrolyzed stream into an expanded gaseous cooled pyrolyzed stream and demethanizing the expanded gaseous cooled pyrolyzed stream in a demethanizer column. An embodiment of the disclosure is one, any or all of prior embodiments in this paragraph up through the first embodiment in this paragraph further comprising compressing a demethanizer side stream to provide compressed side stream, cooling the compressed side stream in the pyrolysis cold box to provide a cooled compressed side stream and refluxing the cooled compressed side stream to the demethanizer column. An embodiment of the disclosure is one, any or all of prior embodiments in this paragraph up through the first embodiment in this paragraph further comprising cooling a demethanized overhead stream from the demethanizer column by heat exchange with a methane stream to provide a condensed demethanized overhead stream and a warm methane stream and separating the condensed demethanized overhead stream in a hydrogen-methane separator to provide a methane stream and a hydrogen stream. An embodiment of the disclosure is one, any or all of prior embodiments in this paragraph up through the first embodiment in this paragraph further comprising mixing a portion of the hydrogen stream with the methane stream before the cooling step to provide a volatile methane stream which is heat exchanged with the demethanized overhead stream to provide the warm methane stream and the condensed demethanized overhead stream. An embodiment of the disclosure is one, any or all of prior embodiments in this paragraph up through the first embodiment in this paragraph further comprising cooling the demethanized overhead stream from the demethanizer column by heat exchange also with the hydrogen stream to provide a warm hydrogen stream. An embodiment of the disclosure is one, any or all of prior embodiments in this paragraph up through the first embodiment in this paragraph further comprising heating the warm methane stream by heat exchange in the pyrolysis cold box. An embodiment of the disclosure is one, any or all of prior embodiments in this paragraph up through the first embodiment in this paragraph further comprising heating the warm hydrogen stream by heat exchange in the pyrolysis cold box.

A second embodiment of the disclosure is a process for separating methane from ethane comprising cooling a hydrocarbon stream; separating the hydrocarbon stream into a gaseous hydrocarbon stream; expanding the gaseous hydrocarbon stream into an expanded gaseous hydrocarbon stream; demethanizing the expanded gaseous hydrocarbon stream in a demethanizer column to provide an overhead stream rich in methane and a bottom stream rich in ethane. An embodiment of the disclosure is one, any or all of prior embodiments in this paragraph up through the second embodiment in this paragraph further comprising compressing a demethanizer side stream to provide compressed side stream, cooling the compressed side stream in a cold box to provide a cooled compressed side stream and refluxing the cooled compressed side stream to the demethanizer column. An embodiment of the disclosure is one, any or all of prior embodiments in this paragraph up through the second embodiment in this paragraph further comprising cooling a demethanized overhead stream from the demethanizer column by heat exchange with a methane stream to provide a condensed demethanized overhead stream and a warm methane stream and separating the condensed demethanized overhead stream in a hydrogen-methane separator to provide a methane stream and a hydrogen stream. An embodiment of the disclosure is one, any or all of prior embodiments in this paragraph up through the second embodiment in this paragraph further comprising mixing a portion of the hydrogen stream with the methane stream before the cooling step to provide a volatile methane stream which is heat exchanged with the demethanized overhead stream to provide the warm methane stream and the condensed demethanized overhead stream. An embodiment of the disclosure is one, any or all of prior embodiments in this paragraph up through the second embodiment in this paragraph further comprising cooling the demethanized overhead stream from the demethanizer column by heat exchange also with the hydrogen stream to provide a warm hydrogen stream. An embodiment of the disclosure is one, any or all of prior embodiments in this paragraph up through the second embodiment in this paragraph further comprising heating the warm methane stream and the warm hydrogen stream by heat exchange in the cold box.

A third embodiment of the disclosure is an apparatus for cooling stream comprising a dehydrogenation reactor; a pyrolysis reactor; and a dehydrogenation cold box in downstream communication with the dehydrogenation reactor; a pyrolysis cold box in downstream communication with the pyrolysis reactor; a refrigerant compressor; the pyrolysis cold box and the dehydrogenation cold box in downstream communication with the refrigerant compressor. An embodiment of the disclosure is one, any or all of prior embodiments in this paragraph up through the third embodiment in this paragraph further comprising a stripping column in downstream communication with the dehydrogenation cold box and a demethanizer column in downstream communication with the pyrolysis cold box and the stripping column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for cooling streams comprising:
cooling a dehydrogenated stream in a dehydrogenation cold box to provide a cooled dehydrogenated stream;
cooling a pyrolyzed stream in a pyrolysis cold box to provide a cooled pyrolyzed stream;
providing a refrigerant stream to the dehydrogenation cold box and to the pyrolysis cold box;
demethanizing said cooled pyrolyzed stream in a demethanizer column to provide a demethanizer side stream;
compressing said demethanizer side stream to provide a compressed side stream;
cooling said compressed side stream in said pyrolysis cold box to provide a cooled compressed side stream; and
refluxing the cooled compressed side stream to said demethanizer column.

2. The process of claim 1 further comprising compressing said refrigerant stream in a first compressor to provide a first compressed refrigerant stream taking a dehydrogenation refrigerant stream from said first compressed refrigerant stream, and heat exchanging said dehydrogenated stream with said dehydrogenation refrigerant stream.

3. The process of claim 2 further comprising taking a second compression refrigerant
stream from said first compressed refrigerant stream and compressing said second compression
refrigerant stream to provide a second compressed refrigerant stream and heat exchanging said
pyrolyzed stream with said second compressed refrigerant stream.

4. The process of claim 1 further comprising separating said cooled dehydrogenated
stream into a net gas stream and a liquid dehydrogenation stream and stripping said liquid
dehydrogenation stream to provide a stripping overhead stream.

5. The process of claim 4 further comprising separating the cooled pyrolyzed stream into a gaseous cooled pyrolyzed stream, expanding said gaseous cooled pyrolyzed stream into an expanded gaseous cooled pyrolyzed stream and demethanizing said expanded gaseous cooled pyrolyzed stream and said stripping overhead stream in a demethanizer column.

6. The process of claim 1 further comprising separating the cooled pyrolyzed stream into a gaseous cooled pyrolyzed stream, expanding said gaseous cooled pyrolyzed stream into an expanded gaseous cooled pyrolyzed stream and demethanizing said expanded gaseous cooled pyrolyzed stream in a demethanizer column.

7. The process of claim 6 further comprising cooling a demethanized overhead stream from said demethanizer column by heat exchange with a methane stream to provide a condensed demethanized overhead stream and a warm methane stream and separating said condensed demethanized overhead stream in a hydrogen-methane separator to provide a methane stream and a hydrogen stream.

8. The process of claim 7 further comprising mixing a portion of said hydrogen stream with said methane stream before said cooling step to provide a volatile methane stream which is heat exchanged with said demethanized overhead stream to provide said warm methane stream and said condensed demethanized overhead stream.

9. The process of claim 7 further comprising cooling said demethanized overhead stream from said demethanizer column by heat exchange also with said hydrogen stream to provide a warm hydrogen stream.

10. The process of claim 7 further comprising heating said warm methane stream by heat exchange in said pyrolysis cold box.

11. The process of claim 9 further comprising heating said warm hydrogen stream by heat exchange in said pyrolysis cold box.

12. The process of claim 7 further comprising heating said warm methane stream and said warm hydrogen stream by heat exchange in said cold box.

13. A process for separating methane from ethane comprising:
cooling a hydrocarbon stream;
separating said hydrocarbon stream into a gaseous hydrocarbon stream;
expanding said gaseous hydrocarbon stream into an expanded gaseous hydrocarbon stream;
demethanizing said expanded gaseous hydrocarbon stream in a demethanizer column to provide an overhead stream rich in methane and a bottom stream rich in ethane;
compressing a demethanizer side stream to provide a compressed side stream;
cooling said compressed side stream in a cold box to provide a cooled compressed side stream; and
refluxing the cooled compressed side stream to said demethanizer column.

14. The process of claim 13 further comprising cooling a demethanized overhead stream from said demethanizer column by heat exchange with a methane stream to provide a condensed demethanized overhead stream and a warm methane stream and separating said condensed demethanized overhead stream in a hydrogen-methane separator to provide a methane stream and a hydrogen stream.

15. The process of claim 14 further comprising mixing a portion of said hydrogen stream with said methane stream before said cooling step to provide a volatile methane stream which is heat exchanged with said demethanized overhead stream to provide said warm methane stream and said condensed demethanized overhead stream.

16. The process of claim 14 further comprising cooling said demethanized overhead stream from said demethanizer column by heat exchange also with said hydrogen stream to provide a warm hydrogen stream.

17. An apparatus for cooling stream comprising:
a dehydrogenation reactor;
a pyrolysis reactor;
a dehydrogenation cold box in downstream communication with said dehydrogenation reactor;
a pyrolysis cold box in downstream communication with said pyrolysis reactor;
a refrigerant compressor;
said pyrolysis cold box and said dehydrogenation cold box in downstream communication with said refrigerant compressor;
a demethanizer column in downstream communication with said pyrolysis cold box; and a demethanizer column side stream outlet in fluid communication with a side compressor and the side compressor in fluid communication with said pyrolysis cold box.

18. The apparatus of claim 17 further comprising a stripping column in downstream communication with said dehydrogenation cold box and a demethanizer column in downstream communication with said pyrolysis cold box and said stripping column.

* * * * *